(12) United States Patent
Rapp et al.

(10) Patent No.: US 6,640,613 B2
(45) Date of Patent: Nov. 4, 2003

(54) METHOD FOR PRODUCING SURFACE ACOUSTIC WAVE SENSORS AND SUCH A SURFACE ACOUSTIC WAVE SENSOR

(75) Inventors: Michael Rapp, Eppelheim (DE); Ullrich Stahl, Karlsruhe (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 10/117,068

(22) Filed: Apr. 1, 2002

(65) Prior Publication Data

US 2002/0113521 A1 Aug. 22, 2002

Related U.S. Application Data

(63) Continuation-in-part of application No. PCT/EP00/09008, filed on Sep. 15, 2000.

(30) Foreign Application Priority Data

Oct. 15, 1999 (DE) .......................................... 199 49 738

(51) Int. Cl.⁷ .............................................. G01N 29/02
(52) U.S. Cl. ..................................... 73/24.01; 73/24.06
(58) Field of Search .............................. 73/24.01, 24.06

(56) References Cited

U.S. PATENT DOCUMENTS

| 4,312,228 A | | 1/1982 | Wohltjen | |
|---|---|---|---|---|
| 4,921,723 A | * | 5/1990 | Nichols et al. | 427/41 |
| 5,702,775 A | * | 12/1997 | Anderson et al. | 428/1 |
| 5,767,687 A | * | 6/1998 | Geist | 324/664 |
| 5,861,677 A | * | 1/1999 | You et al. | 257/783 |
| 6,185,801 B1 | * | 2/2001 | Kadota et al. | 29/25.35 |
| 6,335,224 B1 | * | 1/2002 | Peterson et al. | 438/114 |
| 2002/0032414 A1 | * | 3/2002 | Ragheb et al. | 604/265 |

FOREIGN PATENT DOCUMENTS

| JP | 2-92009 | * 3/1990 | ................. 333/193 |
|---|---|---|---|
| JP | 02-166909 | 6/1990 | ................. 333/193 |
| JP | 10-290138 | * 10/1998 | |
| WO | 02975 | 3/1991 | |

* cited by examiner

*Primary Examiner*—Daniel S. Larkin
(74) *Attorney, Agent, or Firm*—Klaus J. Bach

(57) ABSTRACT

In a method for producing surface wave sensors on the basis of a surface wave building component a polymer parylene film with a thickness of 20 to 200 nm is applied to a hydrophilic sensor surface of the surface wave building component by deposition from the gas phase, whereby the hydrophilic sensor surface becomes hydrophobic, the surface is then subjected to plasma activation to render it hydrophilic and a hydrophilic sorption polymer layer is then applied to the parylene film so as to provide a surface wave sensor with a homogenous sorption polymer layer.

6 Claims, 2 Drawing Sheets

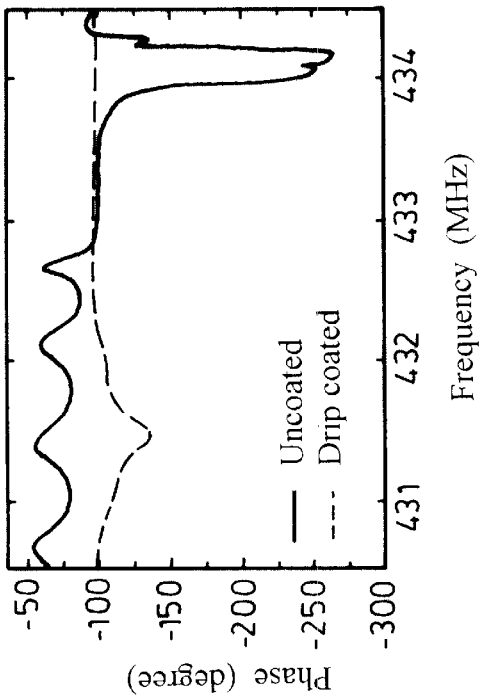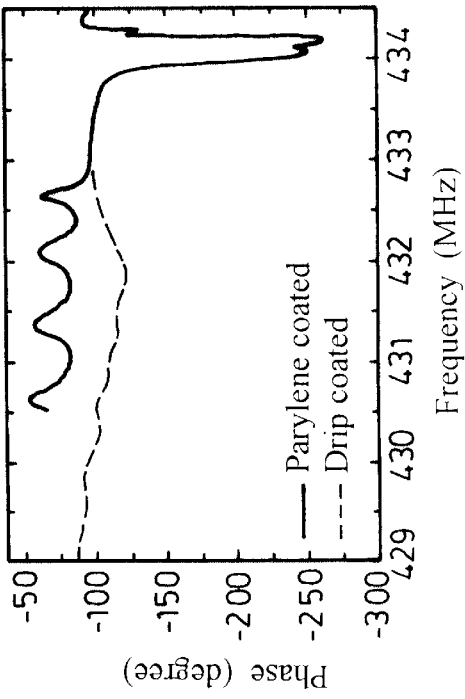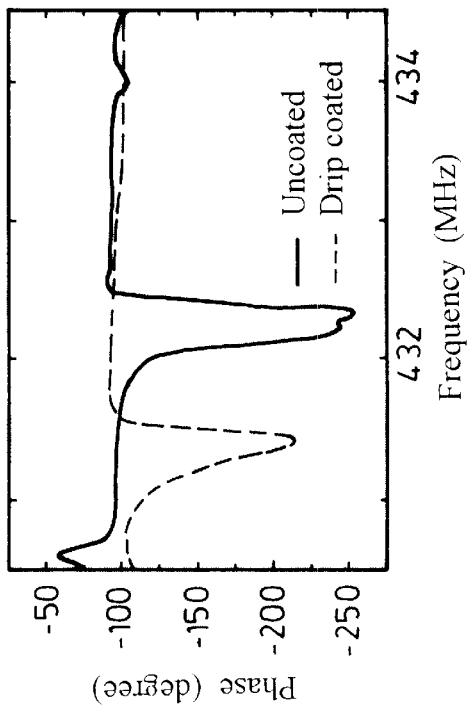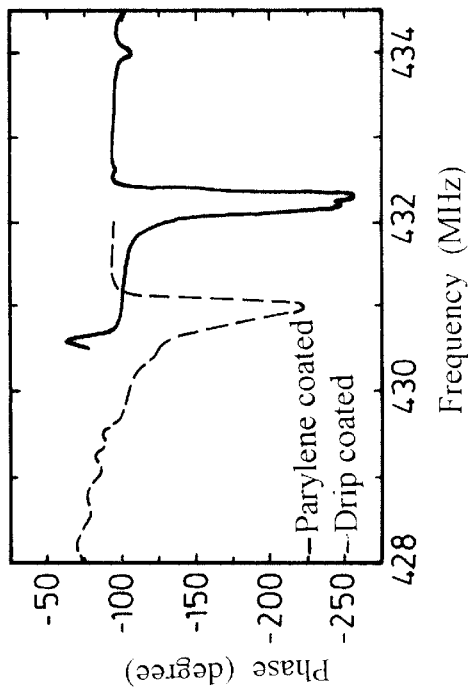

METHOD FOR PRODUCING SURFACE ACOUSTIC WAVE SENSORS AND SUCH A SURFACE ACOUSTIC WAVE SENSOR

This is a continuation-in-part application of international application PCT/EP00/09008 filed Sep. 15, 2000 and claiming the priority of German application 199 49 738.9 filed Oct. 15, 1999.

BACKGROUND OF THE INVENTION

The invention relates to a method for producing surface acoustic wave sensors on the basis of surface acoustic wave components and to a surface acoustic wave sensor.

The use of surface acoustic wave components as gas sensors was originally proposed by Wohltjen who examined this measuring technique(Wohltjen, H., Dessey, R.: Surface acoustic wave probe for chemical analysis"; Anal. Chem. 51 (1979) 1458–1464). These Surface Wave (OFW) building elements which were actually developed as miniaturized high frequency filters find increasing interest for use as chemical and biochemical sensors (Rapp, N.; Barie, N.; Stier, S.; Ache, H.J.; "Optimization of an analytical SAW microsystem for organic gas detection"; Proc. IEEE Ultrasonic. Symp. (1995) 477–490). As sensor property, the mass-sensitive behavior of such components is utilized by applying a coating which is selective for the material to be sensed and the component is the frequency determining element of an oscillator resonant circuit.

In a surface wave component, interdigital transducers are disposed on the piezo-electric substrate of the building component. By the application of a high frequency AC voltage, the transmitter transducer is caused to vibrate. The surface wave generated thereby moves over the substrate and is converted, by the piezo effect, in the receiver transducer into an electrical alternating field. By way of an amplifier, which compensates for the losses resulting from the attenuation of the acoustic wave, the electrical signal is again fed into the transmitter transducers. In this way, an oscillation with a specific resonance frequency, which is based on the travel time of the acoustic and electric wave, occurs in the oscillation circuit. This frequency is uncoupled from the circuit as a measuring signal.

The propagation velocity of the surface wave depends on the character of the surface. If the piezo electric substrate is provided with a thin selective coating the acoustic velocity is changed and, as a result, the resonance frequency of the oscillator circuit is changed.

If an analyte sample is applied to the coated component, a sorption of the analyte occurs in the layer whereby the mass of the building component is increased. As a result, the acoustic velocity is again changed which results in a measurable change of the oscillation frequency. Since frequencies can be measured very accurately, already very small changes of the mass charge of the surface wave building component can be detected.

During the coating of the surface wave sensor with a viscous sorption polymer, the cross-linkages of the sensor surface are often destroyed by the sorption polymer. This results in a non-uniform sorption polymer layer on the substrate and, because of an excessive attenuation caused thereby, in a drastic deterioration of the sensor sensitivity.

It is the object of the present invention to provide a method, which permits the manufacture of a homogeneous sorption polymer layer and a sensor with a homogeneous sorption polymer layer.

SUMMARY OF THE INVENTION

In a method for producing a surface wave sensor on the basis of a surface wave building component a polymer parylene film with a thickness of 20 to 200 nm is applied to a hydrophilic sensor surface of the surface wave building component by deposition from the gas phase, whereby the hydrophilic sensor surface becomes hydrophobic, the surface is then subjected to plasma activation to render it hydrophilic and a hydrophilic sorption polymer layer is then applied to the parylene film by spray coating or drip coating.

The invention has the following advantages:

Because of the better wetting of the sensor surface by the sorption polymers, less complicated coating techniques such as drip coating can be utilized. The improved wetting results in a more uniform deposition of the sorption polymer and, consequently, in a lower attenuation than can be obtained with a non-uniform layer of the same amount of the same polymer. The sensitivity of the sensor can therefore be increased by increasing the layer thickness of the sorption polymer up to a critical attenuation. With the improved wetting also the aging behavior of the sensor is positively affected.

Below, the invention will be described in greater detail on the basis of examples with reference to the drawings.

BRIEF DESCRIPTION OF THE DRAWINGS

FIGS. 2 and 3 show phase curves of sensors with two different sorption polymer layers with, and without, an intermediate parylene layer.

DESCRIPTION OF PREFERRED EMBODIMENTS

Figure 1:
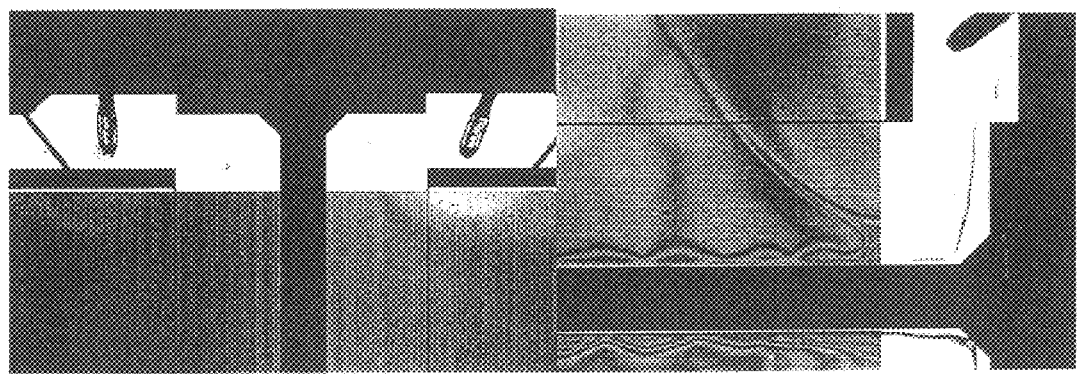
FIG. 1 shows the wetting properties of a sensor coated with parylene and of an uncoated sensor.

With the deposition of a parylene film with a thickness of about 20–50 nm on the OFW surface, a polymer interface layer is formed for the adaptation of the surface tension to the sorption polymer (generally hydrophobic) to be deposited with little increased attenuation (about 1 dB with a 50 nm layer thickness) of the OFW-component. For improving the wetting of polar and, consequently, hydrophilic sorption polymers, the interface layer can be made hydrophilic by a short plasma treatment (<5 min.). Since the plasma treatment is effective only at the surface of the polymer film, the hydrophobic barrier properties thereof remain effective.

With the use of the parylene film with a thickness of between 50 and 200 nm, the use of acid/aggressive polymer has become possible, which, as a result of the barrier properties of the parylene, can no longer corrode the sensor surface or, respectively, the interdigital transducer necessary for the in-coupling and out-coupling of the energy.

Hydrophilic sorption polymers are for example polyisobutylene, polydimethylsiloxane or phenylmethylsiloxane and hydrophilic sorption polymers are for example PEG (PolyEthyleneGlycol) or PVA (PolyVinylAlcohol).

With the use of non-corrosive sorption polymers or when measuring in inert media, the thickness of the parylene layer may be between 20 and 30 nm.

The use of parylene as coating material fulfills two particular purposes:

A thin, uniform polymer film with a low surface tension forms an adhesion improving intermediate layer between the substrate and the sorption polymers and prevents the destruction of cross-links.

Because of its barrier properties, the parylene film protects the OFW component from corrosive effects of acidic and basic sorption polymers or aggressive analytes, or respectively, atmospheres.

Parylenes form a family of linear partially crystalline not cross-linked polymers with interesting properties and various utilization possibilities.

The most simple representative, parylene N (p-xylylene), consists of a linear polymer chain with 1.4-ethylene-bridged phenyl rings.

Besides the parylene N also the chlorinated variants parylene C and parylene D have wide industrial applications because of their lower permeability.

For the coating of thin substrates with thin films of parylenes special vacuum apparatus are required. They consist of three subsequent interconnected chambers with different temperature and pressure conditions.

A certain measured amount of the dimer is placed into the vaporization chamber, the apparatus is evacuated and the educt is subjected to sublimation at 160° C. and a pressure of 1 mbar. The vapor generated in this way reaches the pyrolysis oven in which the dimer is split, at 690° C., into reactive monomers.

The monomer molecules condense in the third chamber at room temperature uniformly on all surfaces and polymerize rapidly to a transparent pore-free film.

In contrast to the industrial procedure wherein generally parylene layers with a thickness of 3 to 15 μm are deposited, the coating process is optimized in this case to the substantially smaller layer thicknesses of 2–200 nm.

One of the reasons for the use of parylene films in OFW sensor systems resides in the adaptation of the surface energy of the sensor to that of the sorption polymers. The deposited film should, as intermediate layer, ideally have a good adhesion to the substrate as well as a low surface energy in order to improve the wetting properties of viscous polymers.

For the examination of the wetting behavior of sorption polymers of sensors, which are provided with a thin parylene layer in comparison with uncoated sensors, the following experiments were performed.

To this end a drop (1.5 μl) of the same polymer solution was placed and dried on the surface of each of several uncoated and parylene-coated sensors. For a comparison of the phase curve changes caused by the coating, the components were characterized before and after the coating by means of a network analyzer.

FIG. 1 shows a microscope photography of two OFW sensors drip-coated by the sorption polymer 1. The left picture shows the good wetting properties of the parylene-coated sensors, the picture at the right indicates the inadequate wetting properties of the untreated sensor.

For the sensors pretreated with parylene, the wetting of the sensor surface with the sorption polymer is found to be excellent. In comparison, the wetting behavior of the untreated sensor is substantially worse. At the right end of the picture of FIG. 1, it can clearly be seen that the polymer deposited collects at the edges of the active structure of the OFW sensor and that the intermediate surface area is not wetted.

FIG. 2 shows the changes of the phase curve by drip-coating with the sorption polymer 1. The left diagram FIG. 2a shows the phase curves of the sensor with the parylene intermediate layer, the right diagram FIG. 2b shows those of the sensor without such intermediate layer. With elimination of the cross-links occurring at the sensor surface not coated with parylene by the sorption polymer, the sorption polymer collects preferably near the active interdigital structures and, consequently, at the location of the largest mass sensitivity of the sensor. In this way, however, a greater layer thickness than actually present is simulated which explains the greater shifting of the phase curve to lower frequencies (see FIGS. 2b, right picture).

The comparison of the two diagrams of FIG. 2 clearly shows the better phase behavior of the OFW sensor pretreated with parylene. The phase reserve remaining after the drip-coating (=difference between phase minimum and phase operating point of the oscillator electronics) is substantially larger. The small frequency displacement caused by the coating with the same amount of polymer deposited can be explained by its more uniform distribution on the sensor surface. The comparison of the microscope photograph of the two drip-coated sensors in FIG. 1 explains the difference between the sensor properties found in FIG. 2.

FIG. 3 shows the change of the phase curve occurring by drip-coating with the sorption polymer 2. The left diagram, FIG. 3a, shows the phase curves of the sensor with the intermediate parylene layer, the right diagram FIG. 3b shows the phase curve of the sensor without intermediate parylene layer.

In comparison with the phase curves of the sensors according to FIG. 2, the sensor obtained by drip-coating of the untreated sensor with this sorption polymer is not usable. In contrast, after the drip-coating of the parylene-treated sensor with this polymer, there remains a substantial phase reserve. The examination of the sensors by a microscope shows also in this case, that the pretreated sensor has a uniform layer thickness but the untreated sensor shows a destruction of the cross-links in the area between the two active interdigital structures which explains the phase behavior of this sensor.

The sorption polymer 1 is butylacrylate-ethyl-acrylate copolymer and the sorption polymer 2 is polyurethane, which is linearly cross-linked.

Particularly advantageous example for the thickness of the two layers:

Parylene either as thin as possible (adhesion provider about 20–50 nm) or as thick as bearable (corrosion-protection, up to 200 nm).

Particularly suitable OFW building component:

The coating was tested among others with: 380 MHz shear wave building component of lithium-tantalate and 433.92 MHz Rayleigh-wave building components (both of quartz). The protection effect and increased wetting by the parylene is universal; it cannot be limited to a particular component. The difference resides only in the maximally applicable layer thickness of the parylene for the different building components since this results in different insertion attenuations.

The results which can be achieved by the use of the parylene as a thin intermediate layer can be summarized as follows:

The intermediate layer acts as an adhesion provider between the inorganic substance surface and the sorption polymer by lowering the surface energy of the sensor. In this way, on one hand, the wetting properties and, on the other hand, the aging behavior of the sensors are substantially improved. Any desired sorption polymers may now be used without the need to fear destruction of the cross-links.

With the application of the parylene film, a diffusion barrier for corrosive materials is formed which protects the sensor from aggressive ambient influences. At the same time, the effect of a signal reversal upon the application of samples with analytes of different polarity is prevented, since the respective analyte can no longer reach the surface of the sensor substrate.

Because the wetting properties are improved by the parylene intermediate layer, the pretreated sensors may be coated by means of the relatively simple drip-coating process.

The good wetting of the parylene-coated sensors with sorption polymers facilitates the coating of the sensors up to the critical phase reserve and consequently results in the achievement of a maximal sensitivity of the respective sensors.

What is claimed is:

1. A method for producing surface wave sensors on the basis of a surface wave building component comprising the following steps:

applying a polymer parylene film with a thickness of 20 to 200 nm to a sensor surface of the surface wave building component which is hydrophilic, by deposition from the gas phase, whereby the hydrophilic sensor surface becomes hydrophobic, rendering the parylene film surface hydrophilic by plasma activation, and depositing on the parylene film a hydrophilic sorption polymer layer by spray coating or drip-coating.

2. A method according to claim 1, wherein the thickness of the parylene film is between 20 and 50 nm.

3. A method according to claim 1, wherein, before the application of the parylene film, the surface of the surface wave building component is silanized with γ-methacryloxypropyltri-methoxysilane as a monolayer.

4. A surface wave sensor on the basis of surface wave building components, having a polymer parylene film with a thickness of between 20 and 200 nm on a surface of the surface wave building component, which is applied by deposition from the gas phase, and a hydrophilic sorption polymer layer on the parylene film, which is applied by spray coating or drip-coating after the parylene film has been hydrophilized by means of plasma activation.

5. A surface wave sensor according to claim 4, wherein the thickness of the parylene layer is between 20 and 50 μm.

6. A surface wave sensor according to claim 4, wherein, before the application of the parylene film, the surface of the surface wave building component is silanized by a monolayer of γ-methacryloxypropyl-trimethoxysilane.

* * * * *